(12) United States Patent
Wagenhals (10) Patent No.: US 9,027,565 B2
(45) Date of Patent: May 12, 2015

(54) INLINE VAPOR COOLING AND FILTERING APPARATUS

(76) Inventor: John Jason Wagenhals, Boca Raton, FL (US)

( * ) Notice: Subject to any disclaimer, the term of this patent is extended or adjusted under 35 U.S.C. 154(b) by 1016 days.

(21) Appl. No.: 13/118,729

(22) Filed: May 31, 2011

(65) Prior Publication Data

US 2012/0000478 A1    Jan. 5, 2012

Related U.S. Application Data

(60) Provisional application No. 61/396,603, filed on Jun. 1, 2010.

(51) Int. Cl.
| | |
|---|---|
| *A24F 47/00* | (2006.01) |
| *A24F 13/04* | (2006.01) |
| *A61M 11/04* | (2006.01) |
| *A61M 16/10* | (2006.01) |
| *A61M 16/16* | (2006.01) |

(52) U.S. Cl.
CPC .............. *A24F 13/04* (2013.01); *A61M 11/041* (2013.01); *A61M 16/105* (2013.01); *A61M 16/1075* (2013.01); *A61M 16/16* (2013.01); *A61M 2205/3606* (2013.01); *A61M 2205/75* (2013.01)

(58) Field of Classification Search
CPC ... A24F 13/04; A61M 11/041; A61M 16/105; A61M 2205/75; A61M 16/16; A61M 2205/3606; A61M 16/1075
USPC .......................... 131/270, 273, 175, 187, 173; 128/200.11, 200.12, 200.13
See application file for complete search history.

(56) References Cited

U.S. PATENT DOCUMENTS 4,029,109 A * 6/1977 Kahler ........................... 131/173

* cited by examiner

*Primary Examiner* — Richard Crispino
*Assistant Examiner* — Dionne Walls Mayes
(74) *Attorney, Agent, or Firm* — The Concept Law Group, P.A.; Scott D. Smiley; Yongae Jun (57) ABSTRACT

A vapor inhalation device includes a first body portion defining a first chamber and a second body portion defining a second chamber provided at least partially within the first chamber, where the second body portion has at least one aperture placing the second chamber in fluid communication with the first chamber. An intake conduit defines a first air passageway from an exterior of the first body portion to within the second chamber. An output conduit has a proximal end located within the first chamber, a distal end opposite the proximal end and located at the exterior of the first body portion, is physically coupled to the first body portion at a location different from the proximal end of the output conduit, and defines a second air passageway extending from within the first chamber to the exterior of the body portion.

11 Claims, 5 Drawing Sheets

—PRIOR ART—

INLINE VAPOR COOLING AND FILTERING APPARATUS

CROSS-REFERENCE TO RELATED APPLICATIONS

This application claims priority under 35 U.S.C. §.119(e) based on U.S. Provisional Patent Application Ser. No, 61/396,603, filed Jun. 1, 2010, the contents of which are relied upon and incorporated herein by reference in their entirety.

FIELD OF THE INVENTION

The present invention relates generally to a vaporizer for inhalation of active ingredients within a plant material, and, more particularly, relates to a vapor cooling and filtering apparatus at the output of the vaporizer that provides vapor cooling, filtering, and reduced taste emissions.

BACKGROUND OF THE INVENTION

A vaporizer is a device used to extract the active ingredients of plant material, e.g., cannabis, tobacco, or other herbs or blends, for inhalation by a human. Vaporization involves heating a material so that its active compounds boil off into a vapor. As opposed to smoking, i.e., burning, vaporization avoids the production of irritating, toxic, and carcinogenic by-products. In fact, no combustion occurs, so no smoke or taste of smoke is present.

Studies show that vapor contains substantially zero particulate matter or tar, and, in comparison to smoking, significantly lower concentrations of noxious gases such as carbon monoxide. It has also been shown that, in comparison to other drug delivery methods, such as ingestion, vaporization has a more rapid onset of pharmacological effect, direct delivery into the bloodstream (via the lungs), and more precise titration such that the desired level is reached and not exceeded, enabling consistent and appropriate dosage.

Figure 1:
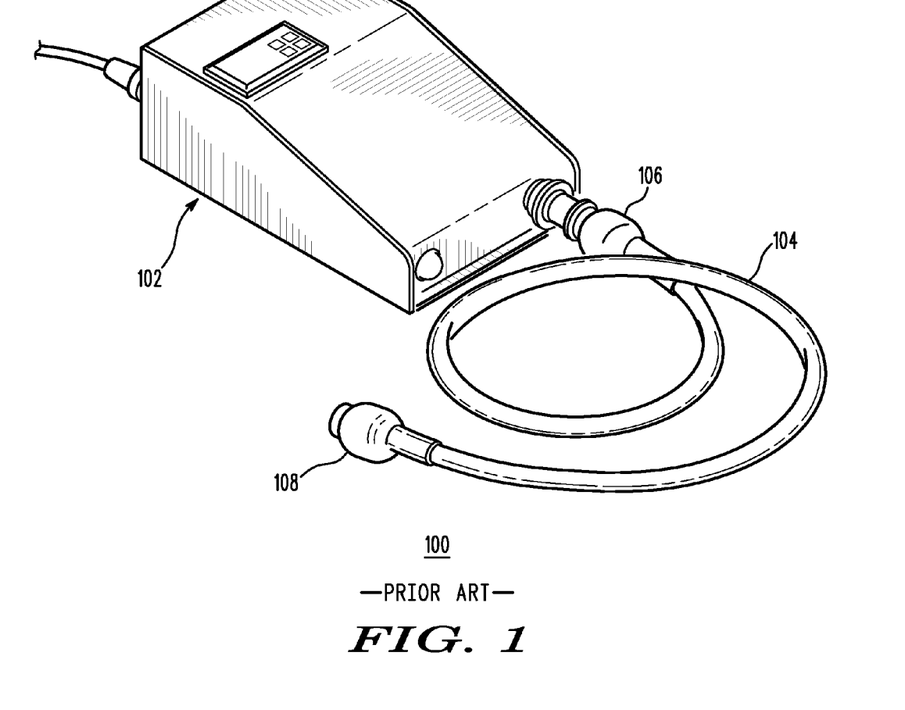
FIG. 1 is a perspective view of a prior-art vaporizer control box, flexible drawtube, and mouthpiece.

Referring now to FIG. 1, one embodiment of a prior-art vaporizer 100 is shown in a perspective view. The prior-art vaporizer 100, as shown in FIG. 1, includes a vaporizer control box 102, a material holder 106, and a vapor inhalation device 104, e.g., a long flexible drawtube ("whip") through which the user inhales the vapor, reducing its temperature on arrival. The inhalation device 104 includes a mouthpiece 108 at its end.

The vapor inhalation device 104 provides an airtight sealed pathway between the material holder 106 and the user's mouth. However, even at the end of the vapor inhalation device 104, the vapor is at a temperature that is still too hot for comfortable ingestion by a human. In addition, the vapor often contains a somewhat unpleasant taste due to the heated air passing over and being heated by the heating element(s) within the vaporizer control box 102, as well as picking up particles, dust, and/or the characteristics of the substance being vaporized and inhaled.

Therefore, a need exists to overcome the problems with the prior art as discussed above.

SUMMARY OF THE INVENTION

The invention provides an inline vapor cooling and filtering apparatus that overcomes the hereinafore-mentioned disadvantages of the heretofore-known devices and methods of this general type and that effectively cools and filters a passing stream of air prior to ingestion by a user. The invention also provides an inline vapor cooling and filtering apparatus that is easy to fill, does not spill its contents, regardless of its position, and is easy to evacuate and clean.

With the foregoing and other objects in view, there is provided, in accordance with the invention, a vapor inhalation device includes a first body portion defining a first chamber and a second body portion defining a second chamber provided at least partially within the first chamber, where the second body portion has at least one aperture placing the second chamber in fluid communication with the first chamber. An intake conduit defines a first air passageway from an exterior of the first body portion to within the second chamber. An output conduit has a proximal end located within the first chamber, a distal end opposite the proximal end and located at the exterior of the first body portion, is physically coupled to the first body portion at a location different from the proximal end of the output conduit, and defines a second air passageway extending from within the first chamber to the exterior of the body portion.

In accordance with one more feature of the present invention, the first body portion has a proximal end and a distal end opposite the proximal end, the intake conduit is provided at the proximal end of the first body portion, and the output conduit is provided at the distal end of the first body portion.

In accordance with yet another feature of the present invention, the second body portion further includes a proximal end physically coupled to the proximal end of the first body portion and surrounding a portion of the intake conduit.

In accordance with a further feature of the present invention, the air passageway is substantially at the proximal end of the second body portion.

In accordance with an additional feature of the present invention, the intake conduit has a distal end located within the second chamber, has a proximal end opposite the distal end and located at the exterior of the first body portion, and is physically coupled to the first body portion at a location different from the distal end of the intake conduit.

In accordance with a further feature of the present invention, the first body portion defines a central axis and the intake conduit and the output conduit have central axes that reside substantially on the central axis of the first body portion.

In accordance with yet another feature of the present invention, at least one of the first body portion, the second body portion, the intake conduit, and the output conduit are of a glass material.

With the foregoing and other objects in view, there is provided, in accordance with the invention, a vapor inhalation device that includes a first body portion having a length and defining a first chamber and a second body portion within the first body portion, where the second body portion has a length at least 40% of the length of the first body portion and defines a second chamber within the first chamber and has at least one aperture placing the second chamber in fluid communication with the first chamber. An elongated intake conduit defines a first air passageway from an exterior of the first body portion to within the second chamber and extending into the second body portion a distance that is at least 25% of the length of the first body portion. An elongated output conduit defining a second air passageway from within the first chamber to the exterior of the body portion, the elongated output conduit extending into the first chamber a distance that is at least 25% of the length of the first body portion.

In accordance with another feature of the present invention, the elongated output conduit has a proximal end located within the first chamber, a distal end opposite the proximal end and located at the exterior of the first body portion, and is physically coupled to the first body portion at a location different from the proximal end of the output conduit.

In accordance with yet another feature of the present invention, the first body portion has a proximal end and a distal end opposite the proximal end, the elongated intake conduit is provided at the proximal end of the first body portion, and the elongated output conduit is provided at the distal end of the first body portion.

In accordance with an additional feature of the present invention, the first body portion has a proximal end and a distal end opposite the proximal end, the elongated intake conduit is provided at the proximal end of the first body portion, and the elongated output conduit is provided at the distal end of the first body portion.

Although the invention is illustrated and described herein as embodied in an inline vapor cooling and filtering apparatus, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the inline vapor cooling and filtering apparatus.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient inline vapor cooling and filtering apparatus that overcomes the hereinafore-mentioned disadvantages of the heretofore-known devices and methods of this general type and that effectively coots and filters a passing stream of air prior to ingestion by a user. The invention also provides an inline vapor cooling and filtering apparatus that is easy to fill, does not spill its contents, regardless of its position, and is easy to evacuate and clean.

Figure 2:
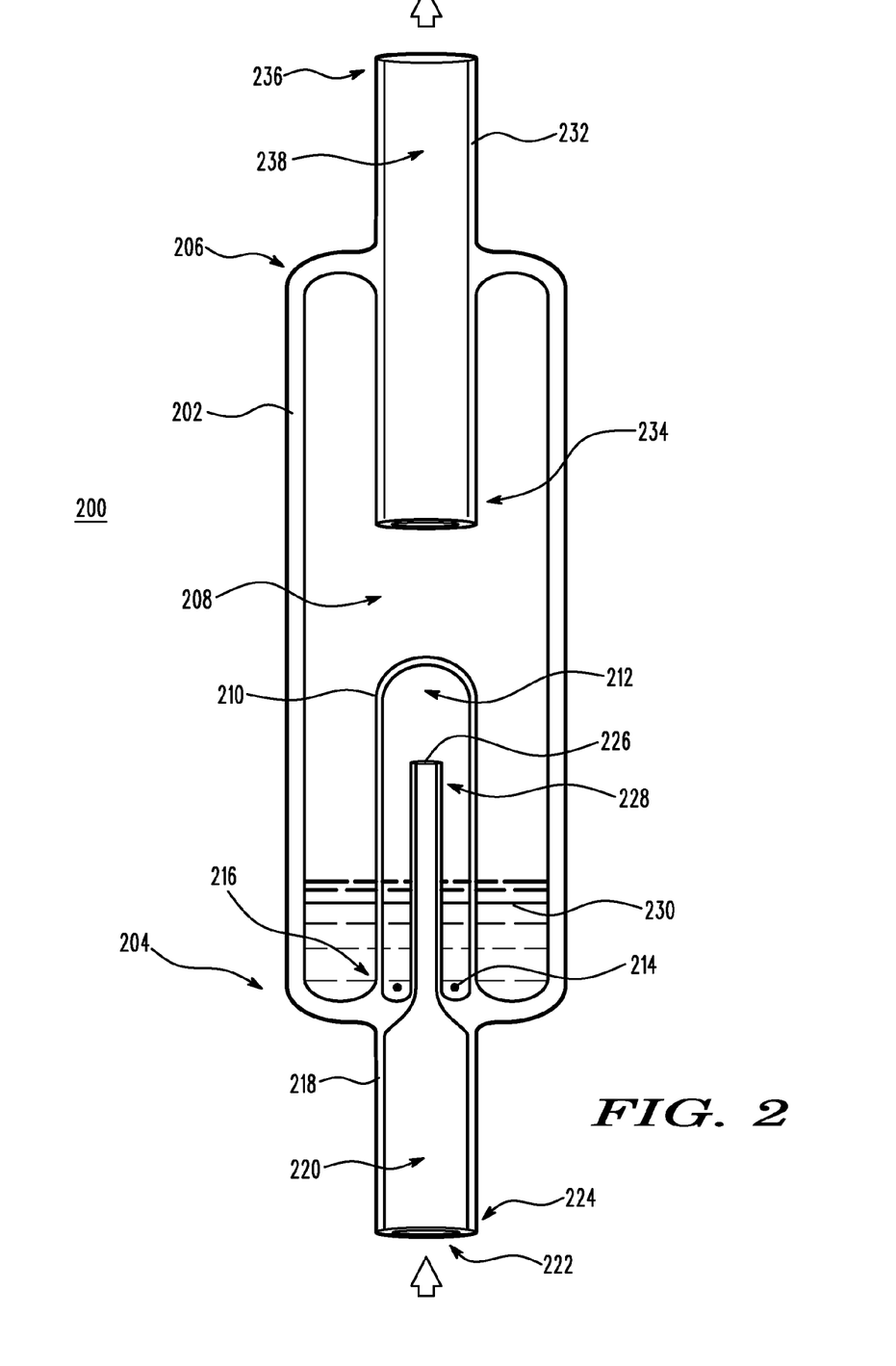
FIG. 2 is cross-sectional devotional view of an inline vapor cooling and filtering apparatus in a vertical orientation in accordance with an exemplary embodiment of the present invention.

Referring now to FIG. 2, one embodiment of the present invention is shown in a cross-sectional side elevational view. The figures of the instant application show several advantageous features of the present invention, but, as will be described below, the invention can be provided in several shapes, sizes, combinations of features and components, and varying numbers and functions of the components. The first example of an inline vapor cooling and filtering apparatus 200, as shown in FIG. 2, includes a main body portion 202 that has a proximal end 204 and a distal end 206 and defines a main chamber 208. The main body portion 202, in accordance with an embodiment of the present invention, is able contain liquid, e.g., water, and is formed of a glass material, e.g., borosilicate glass. The invention, however, is not limited to any particular materials.

Within the main body portion 202 is a secondary body portion 210 which defines a second chamber 212, also within the main chamber 208. The secondary body portion 210 has at least one aperture 214, which places the second chamber 212 in fluid communication with the main chamber 208. In accordance with the embodiment shown in FIG. 2, the secondary body portion 210 has a proximal end 216 that is physically coupled to the proximal end 204 of the main body portion 202 and the at least one aperture 214 is substantially at the proximal end 216 of the secondary body portion 210. In accordance with an embodiment of the present invention, a length $L_2$ of the secondary body portion 210 extending into the main body portion 202 is at least about 40% of the length $L_1$ of the main body portion 202.

An elongated intake conduit 218 is provided at the proximal end 204 of the main body portion 202. The intake conduit 218 serves as the point of coupling between the inline vapor cooling and filtering apparatus 200 and the long flexible drawtube ("whip") 104 shown in FIG. 1.

The intake conduit 218 defines an intake air passageway 220 from an exterior of the main body portion 202 to within the secondary chamber 212. The intake air passageway 220 allows air to enter the secondary chamber 212 and, ultimately the main chamber 208 through the apertures 214. The intake conduit 218 includes an input 222 at its proximal end 224 and an output 226 at its distal end 228, which is located within the secondary body portion 210.

As shown in FIG. 2, the intake conduit 218 is coupled to the main body portion 202 at a location along the intake conduit 218 so that the distal end 228 of the intake conduit 218 extends well within the main body portion 202 (and the secondary body portion 210). In accordance with an embodiment of the present invention, a length L3 of the portion of the intake conduit 218 extending into the main body portion 202 is at least about 25% of the overall length L1 of the main body portion 202.

FIG. 2 also shows the presence of a fluid 230 within both the main chamber 202 and the secondary chamber 212. The fluid 230 is able to pass from the main chamber 202 to the secondary chamber 212 via the apertures 214. As stated above, when the inline vapor cooling and filtering apparatus 200 is in use, the proximal end 224 of the elongated intake conduit 218 is coupled to the flexible drawtube 104. Heated vapor exiting the flexible drawtube 104 enters the input 222 at the proximal end 224 of the elongated intake conduit 218. The vapor then passes along the intake air passageway 220 to the distal end 228 of the elongated intake conduit 218 and exits the output 226 of the elongated intake conduit 218. Once the vapor exits the output 226 of the elongated intake conduit 218, it enters directly into the secondary chamber 212 formed by the secondary body portion 210. The secondary body portion 210 is coupled to the main body portion 202 so that the only passageway for air or water to transfer from within the secondary chamber 212 to the main chamber 208 is through the apertures 214 formed within the secondary body portion 210. In other words, the coupling between the secondary body portion 210 and the main body portion 202 is a fixed watertight connection.

When the inline vapor cooling and filtering apparatus 200 is in the vertical position illustrated FIG. 2, i.e., the distal end 206 is held above the proximal end 204, the vapor exiting the output 226 of the elongated intake conduit 218 must pass through the fluid 230 in order to transfer from the secondary chamber 212 to the main chamber 208. As will be explained below, a vacuum placed upon the main chamber 208 creates a negative pressure within the main chamber 202 and causes the vapor exiting the output 226 of the elongated intake conduit 218 to pass through the fluid 230 within the secondary chamber 212, through the apertures 214, through the fluid 230 within the main chamber 208, and pass through the main chamber 208. Advantageously, the fluid 230 cools the hot vapor as it passes through. In addition, the fluid 230 absorbs particulates in the vapor and serves as a filter to help clean the vapor as it passes through. If desired, flavors can be added to the fluid 230 to enhance the flavor of the vapor received into the user's mouth.

At the distal end of the main body portion 202 is an output conduit 232 that has a proximal end 234 located within the main chamber 208 and a distal end 236 that is opposite the proximal end 234 and located at the exterior of the main body portion 202. The output conduit 232 defines a second air passageway 238 that allows air to pass from within the main chamber 208 to the exterior of the main body portion 202. In accordance with an embodiment of the present invention, the output conduit 232 is physically coupled to the main body portion 202 so that a watertight seal is formed between the output conduit 232 and the main body portion 202. In accordance with a further embodiment of the present invention, the proximal end 234 of the output conduit 232 extends into the main chamber 202 a distance $L_4$ that is at least about 25% of the length $L_1$ of the main body portion 202.

When the inline vapor cooling and filtering apparatus 200 is in use, the proximal end 224 of the elongated intake conduit 218 is coupled to the flexible drawtube 104. A user then places his or her mouth on the distal end 236 of the output conduit 232 and inhales. The inhalation creates a negative pressure within the main chamber 208. This negative pressure transfers through the fluid 230, through the apertures 214 and into the secondary chamber 212. This negative pressure within the secondary chamber 212 causes the vapor to exit the output 226 of the elongated intake conduit 218, pass through the fluid 230 within the secondary chamber 212, through the apertures 214, through the fluid 230 within the main chamber 208, through the main chamber 208, into and through the second air passageway 238, and finally into the mouth of the user. Advantageously, the fluid 230 cools and filters the hot vapor, which carries the organic substance it picked up while passing through the material holding chamber 106. This cooling and filtering provides a much improved experience over prior-art vaporizer devices.

Figure 3:
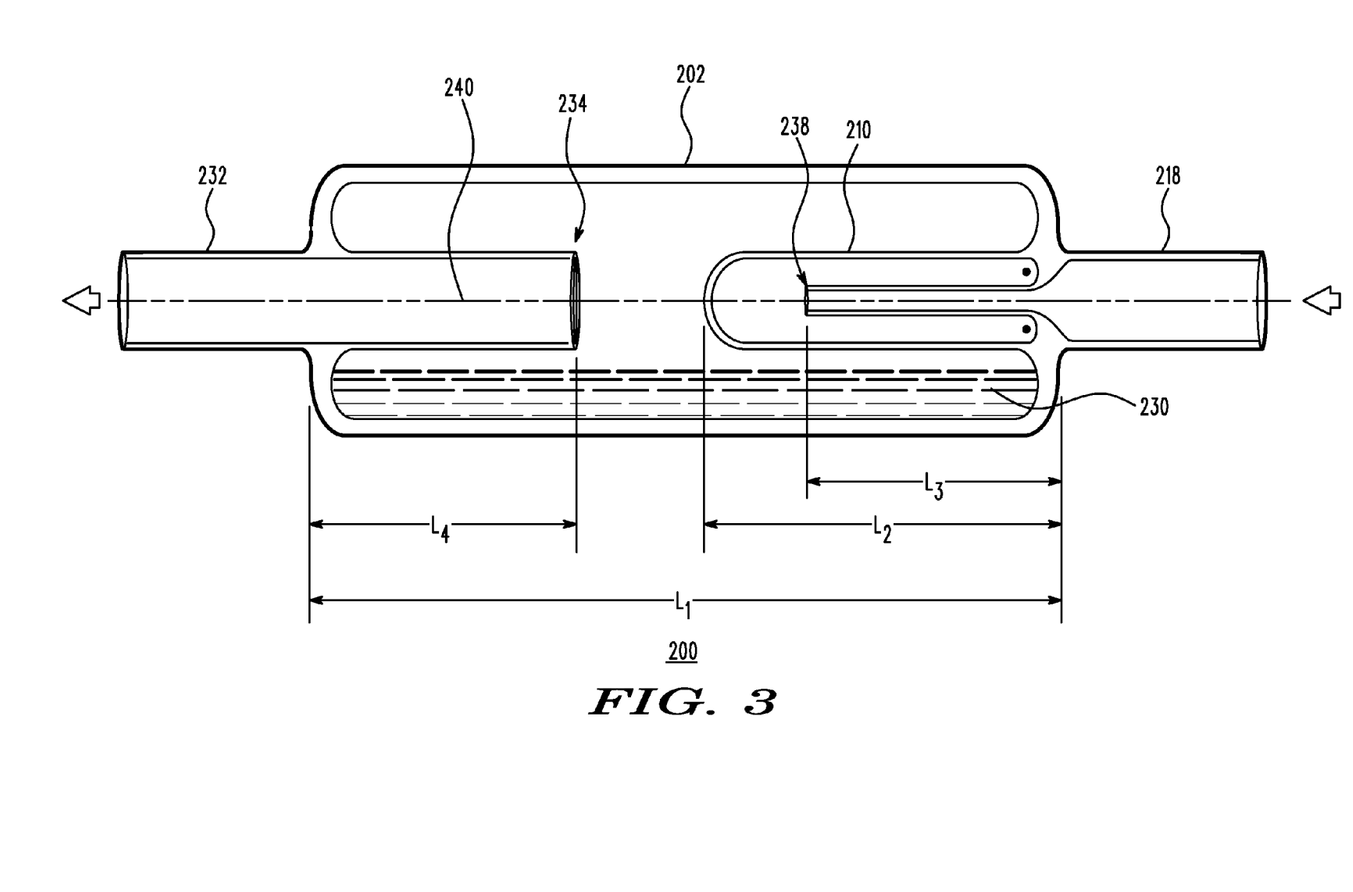
FIG. 3 is a cross-sectional devotional view of the inline vapor cooling and filtering apparatus of FIG. 2 in a horizontal orientation showing that fluid is contained within the apparatus when it is placed on its side in accordance with an exemplary embodiment of the present invention.

In accordance with an embodiment of the present invention, and as is shown in FIG. 3, the main body portion 202 defines a central axis 240. In this embodiment, a central axis of the elongated intake conduit 218 and central axis of the output conduit are substantially collinear with the central axis 240 of the main body portion 202. This alignment is also be seen in the perspective views of FIGS. 4 & 5. This co-alignment between the elements provides the advantage that when one lays the inventive inline vapor cooling and filtering apparatus 200 on its side, the fluid 230 is unable to spill out. This is shown in the horizontal side elevational view of FIG. 3. When on its side, the fluid 230 is unable to reach and enter either the proximal end 234 of the output conduit 232 or the distal end 228 of the intake conduit 218.

The initial filling of the inline vapor cooling and filtering apparatus 200 is performed by holding the inline vapor cooling and filtering apparatus 200 in the vertical orientation shown in FIG. 2 and submerging the proximal end 224 of the intake conduit 218 in a fluid, usually water. A user then simply places their mouth on the distal end 236 of the output conduit 232 and applies suction. The negative pressure caused by the suction will draw the fluid up through the intake conduit 218 and into the secondary chamber 212.

Emptying and cleaning the inline vapor cooling and filtering apparatus 200 is performed by holding the inline vapor cooling and filtering apparatus 200 in the vertical orientation shown in FIG. 2. A user then simply places their mouth on the distal end 236 of the output conduit 232 and blows air into the output conduit 232. The positive pressure caused by the user blowing into the output conduit 232 will force the fluid out of the main chamber 208, through the apertures 214 up through secondary chamber 212, and down the output 226 of the intake conduit 218.

Figures 4, 5:
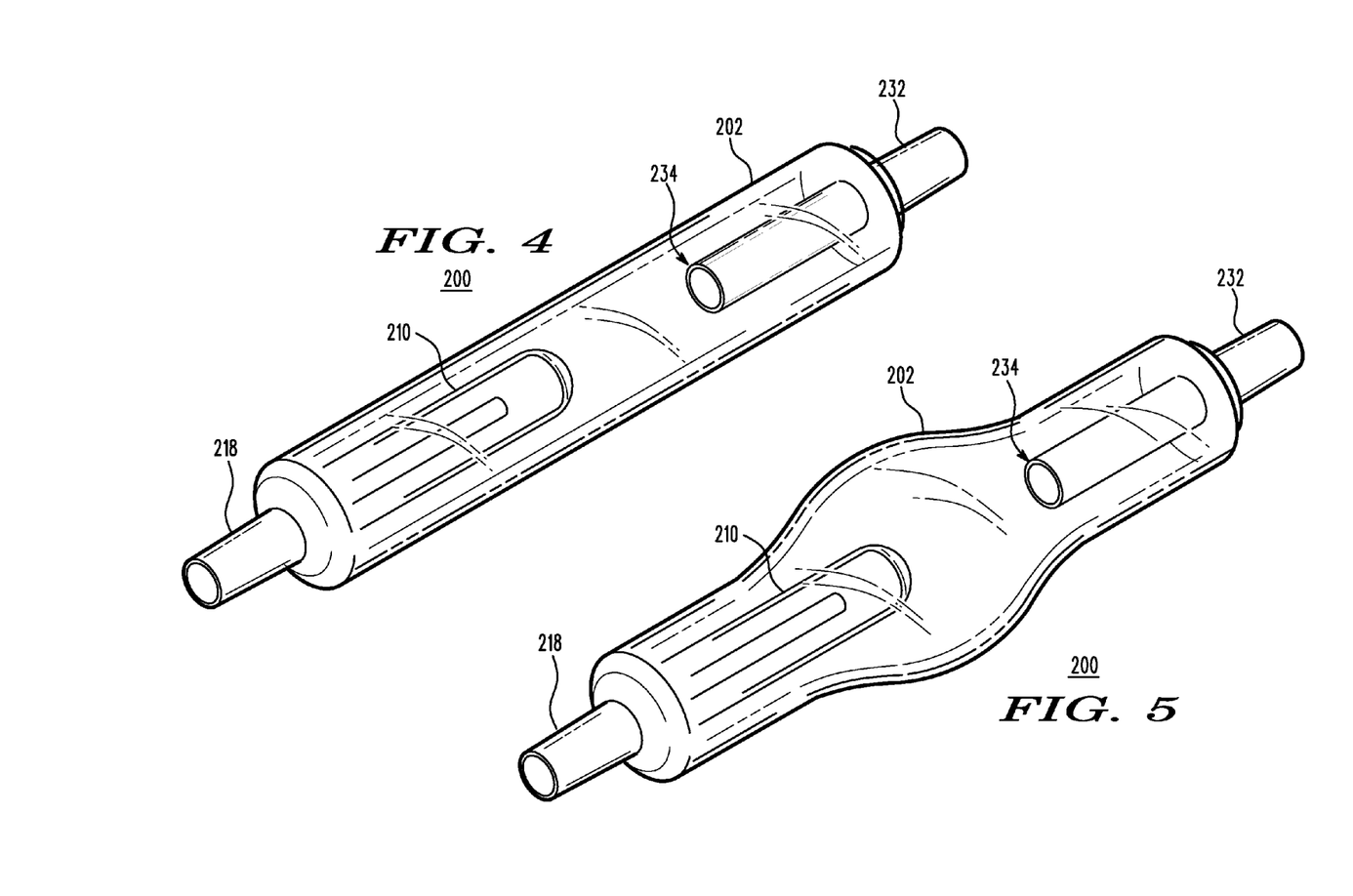
FIG. 4 is a perspective view of the inline vapor cooling and filtering apparatus FIGS. 2 & 3.
FIG. 5 is a perspective view of an inline vapor cooling and filtering apparatus having a body with both cylindrical and bulbous areas in accordance with an exemplary embodiment of the present invention.

It should be noted that the invention is in no way limited to the shapes shown in FIGS. 2-4. For example, the main body portion 202 can be an elongated cylinder, around ball shape, a shape with both cylindrical and round features, as is shown in FIG. 5, and many more. In addition the intake and output conduits can be any shape that provides a channel through which something (fluid and air/vapor) is conveyed. In one embodiment, the overall length of the assembly 200 is about 7.5 inches and the width of the main body portion 202 is about 1.25 inches to about 1.50 inches.

As can be seen in FIGS. 4 & 5, in one embodiment of the present invention, a diameter of the secondary body portion 210 is greater than a diameter of the proximal end 234 of the output conduit 232. This difference in diameter further helps to prevent the liquid 230 from falling off of the surface of the secondary body portion 210 and into the in proximal end 234 of the output conduit 232 when the apparatus 200 is turned upside down, i.e., the intake conduit 218 is placed above the output conduit 232. In accordance with further embodiments of the present invention, the outer diameter of the intake conduit 218 and the outer diameter of the main body portion 202 are substantially equal. In further embodiments, the outer diameter of the output conduit 232 and the outer diameter of the main body portion 202 are substantially equal.

The present invention can alternatively be used in applications other than vaporizers. For example, the present invention can be used in a laboratory environment for cooling gases or vapors through any fluid desired.

Figure 6:
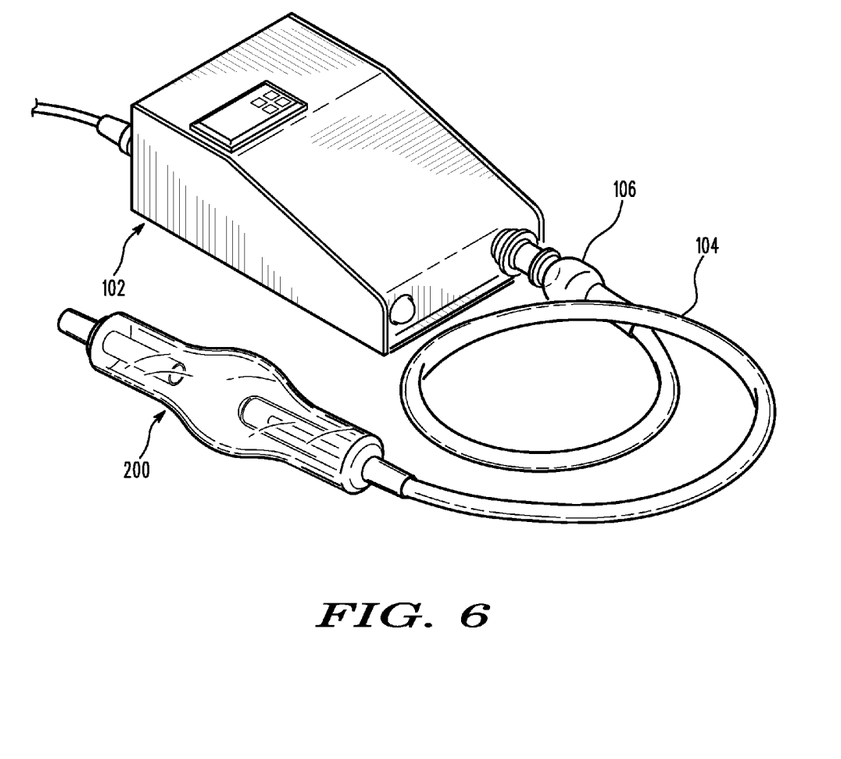
FIG. 6 is perspective view of the inline vapor cooling and filtering apparatus of FIG. 5 coupled to a prior-art drawtube and vaporizer control box.

An inline vapor cooling and filtering apparatus has been disclosed that provides a novel cooling and filtering effect on vapor expelled by a vaporizer device, thus creating the most pure and healthy vapor possible delivered through a completely sealed, non-contaminated vapor passage. FIG. 6 shows the inventive inline vapor cooling and filtering apparatus 200 connected to a vaporizer control box 102 through a drawtube 104, allowing a user to inhale cool, filtered vapor. Advantageously, the apparatus can be held in any position without concern of its cooling liquid being expelled.

What is claimed is:

1. A vapor inhalation device comprising:
    a first body portion defining a first chamber and having a central axis;
    a second body portion defining a second chamber provided at least partially within the first chamber, the second body portion having at least one aperture placing the second chamber in fluid communication with the first chamber;
    an intake conduit defining a first air passageway from an exterior of the first body portion to within the second chamber, the intake conduit having a central axis that resides substantially on the central axis of the first body portion; and
    an output conduit:
        having a proximal end located within the first chamber;
        having a distal end opposite the proximal end and located at the exterior of the first body portion;
        physically coupled to the first body portion at a location different from the proximal end of the output conduit;
        defining a second air passageway extending from within the first chamber to the exterior of the first body portion; and
        having a central axis that resides substantially on the central axis of the first body portion.

2. The vapor inhalation device according to claim 1, wherein:
    the first body portion has a proximal end and a distal end opposite the proximal end; and
    the second body portion further comprises:
        a proximal end physically coupled to the proximal end of the first body portion and surrounding a portion of the intake conduit.

3. The vapor inhalation device according to claim 2, wherein:
    the first air passageway is substantially at the proximal end of the second body portion.

4. The vapor inhalation device according to claim 1, wherein:
    the intake conduit:
        has a distal end located within the second chamber;
        has a proximal end opposite the distal end and located at the exterior of the first body portion; and
        is physically coupled to the first body portion at a location different from the distal end of the intake conduit.

5. The vapor inhalation device according to claim 1, wherein:
    the first body portion is of a watertight material.

6. The vapor inhalation device according to claim 1, wherein:
    at least one of the first body portion, the second body portion, the intake conduit, and the output conduit are of a glass material.

7. A vapor inhalation device comprising:
    a first body portion having a proximal end and a distal end, opposite the proximal end, and defining a first chamber;
    a second body portion defining a second chamber provided at least partially within the first chamber, the second body portion having at least one aperture placing the second chamber in fluid communication with the first chamber;
    an intake conduit provided at the proximal end of the first body portion and defining a first air passageway from an exterior of the first body portion to within the second chamber; and
    an output conduit:
        having a proximal end located within the first chamber;
        having a distal end opposite the proximal end and located at the exterior of the first body portion;
        physically coupled to the first body portion at a location different from the proximal end of the output conduit;
        provided at the distal end of the first body portion, such that the intake conduit is opposite the output conduit; and
        defining a second air passageway extending from within the first chamber to the exterior of the first body portion.

8. The vapor inhalation device according to claim 7, wherein the second body portion further comprises:
    a proximal end physically coupled to the proximal end of the first body portion and surrounding a portion of the intake conduit.

9. The vapor inhalation device according to claim 7, wherein:
    the first air passageway is substantially at the proximal end of the second body portion.

10. The vapor inhalation device according to claim 7, wherein:
    the intake conduit:
        has a distal end located within the second chamber;
        has a proximal end opposite the distal end and located at the exterior of the first body portion; and is physically coupled to the first body portion at a location different from the distal end of the intake conduit.

11. The vapor inhalation device according to claim 7, wherein:
the first body portion is of a watertight material.

* * * * *